(12) United States Patent
Niessen et al.

(10) Patent No.: US 8,872,507 B2
(45) Date of Patent: Oct. 28, 2014

(54) ELECTRONIC DEVICE SUITABLE FOR BIOIMPLANTATION

(75) Inventors: Rogier Adrianus Henrica Niessen, Eindhoven (NL); Willem Franke Pasveer, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 771 days.

(21) Appl. No.: 12/994,168

(22) PCT Filed: May 26, 2009

(86) PCT No.: PCT/IB2009/052199
§ 371 (c)(1), (2), (4) Date: Nov. 23, 2010

(87) PCT Pub. No.: WO2009/147573
PCT Pub. Date: Dec. 10, 2009

(65) Prior Publication Data
US 2011/0101914 A1 May 5, 2011

(30) Foreign Application Priority Data
Jun. 5, 2008 (EP) .................................... 08157658

(51) Int. Cl.
*H02J 7/00* (2006.01)
*G01R 33/00* (2006.01)
*H01M 10/42* (2006.01)
*H01M 10/44* (2006.01)
*H01M 10/46* (2006.01)
*A61N 1/378* (2006.01)

(52) U.S. Cl.
CPC ............ *H01M 10/46* (2013.01); *H01M 10/425* (2013.01); *H01M 10/44* (2013.01); *A61N 1/3787* (2013.01); *Y02E 60/12* (2013.01)

USPC ........... 324/205; 324/200; 324/463; 324/249; 324/244; 324/252; 320/108

(58) Field of Classification Search
USPC .................................. 324/244, 260, 262, 263
See application file for complete search history.

(56) References Cited

U.S. PATENT DOCUMENTS 5,749,909 A 5/1998 Schroeppel et al.
6,067,474 A * 5/2000 Schulman et al. .............. 607/57
(Continued)

FOREIGN PATENT DOCUMENTS

EP 1475879 A2 11/2004
GB 2398176 A 8/2004
(Continued)

OTHER PUBLICATIONS

Gaddam et al: "Remote Power Delivery for Hybrid Integrated Bio-Implantable Electrical Stimulation System"; Smart Structures and Materials 2005: Smart Electronics, MEMS, BIOMEMS, and Nanotechnology, Proceedings of SPIE, May 2005, vol. 5763, pp. 20-31.

(Continued)

*Primary Examiner* — Edward Tso
*Assistant Examiner* — Alexis A Boateng

(57) ABSTRACT

The present application discloses an integrated circuit comprising a circuit portion (100) coupled between first and second power supply lines (110; 120); a first switch (115, 135) coupled between the first power supply line (110, 120) and the circuit portion (100) for disconnecting the circuit portion from the first power supply line during an inactive mode of the circuit portion; and an arrangement (315, 335, 410) for, during said inactive mode, providing the circuit portion (100) with a fraction of its active mode power supply at least when averaged over said inactive mode to prevent the circuit portion voltage to drop below a threshold value. The present application further discloses a method for controlling such an integrated circuit.

20 Claims, 2 Drawing Sheets

(56) References Cited

U.S. PATENT DOCUMENTS

| | | | |
|---|---|---|---|
| 6,178,353 B1 * | 1/2001 | Griffith et al. | 607/61 |
| 6,809,498 B2 | 10/2004 | Nakamura et al. | |
| 6,894,456 B2 * | 5/2005 | Tsukamoto et al. | 320/107 |
| 6,984,902 B1 | 1/2006 | Huang et al. | |
| 6,988,001 B2 * | 1/2006 | Greatbatch et al. | 607/9 |
| 7,573,734 B2 * | 8/2009 | Grino et al. | 365/145 |
| 7,808,236 B1 * | 10/2010 | Huang et al. | 324/249 |
| 7,979,126 B2 * | 7/2011 | Payne et al. | 607/36 |
| 8,236,443 B2 * | 8/2012 | Snyder et al. | 429/136 |
| 2003/0085684 A1 * | 5/2003 | Tsukamoto et al. | 320/108 |
| 2004/0126620 A1 * | 7/2004 | Viehland et al. | 428/692 |
| 2007/0296283 A1 | 12/2007 | Tucker et al. | |

FOREIGN PATENT DOCUMENTS

| | | |
|---|---|---|
| WO | 2007121265 A1 | 10/2007 |
| WO | 2007127106 A2 | 11/2007 |

OTHER PUBLICATIONS

Priya et al: "Recent Advnacements in Magnetoelectric Particulate and Laminate Composites"; Journal of Electroceramics, 2007, vol. 19, pp. 147-164.

Receveur et al: "Microsystem Technologies for Implantable Applications"; Journal of Micromechanics and Engineering, 2007, vol. 17, pp. R50-R080.

Arai et al: "A New Hybrid Device Using Magnetostrictive Amorphous Films"; IEEE Transactions on Magnetics, Mar. 1994, vol. 30, No. 2, pp. 916-918.

Bayrashev et al: "Low Frequency Wireless Powering of Microsystems Using Piezoelectric-Magnetostrictive Laminate Composites"; The 12 International Conference on Solid State Sensors, Actuators and Microsystems, Jun. 2003, pp. 1707-1710.

Ferro Solutions Inc.: "VEH-360 Electromechanical Vibration Energy Harvester"; Description of a Company Product, 2 Page Document, 2007.

* cited by examiner

ELECTRONIC DEVICE SUITABLE FOR BIOIMPLANTATION

FIELD OF THE INVENTION

The invention relates to an electronic device suitable for bioimplantation. The invention also relates to an assembly of an electronic device according to the invention and a charging unit adapted to generate a magnetic field.

BACKGROUND OF THE INVENTION

During the twentieth century, energy consumption increased dramatically and an unbalanced energy management exists. While there is no sign that this growth in demand will abate (particularly amongst the developing nations), there is now an awareness of the transience of non-renewable resources and the irreversible damage caused to the environment. In addition, there is a trend towards the miniaturization and portability of computing and communications devices. These energy-demanding applications require small, light power sources that are able to sustain operation over long periods of time, particularly in remote locations such as space and exploration. Furthermore, advances in medical science are leading to an increasing number of implantable electrically-operated devices, such as pacemakers and bioimplantable sensors. These devices need power supplies that will operate for extremely long durations as maintenance would necessitate surgery. Presently, bioimplantable electronic devices can be wirelessly charged by means of a magnetic field (inductively charged). The known bioimplantable electronic device therefore comprises a (re)chargeable power source and a coil connected to said power source to enable wirelessly charging of the power source by means of a magnetic field (inductively charged). The amount of energy that can be transferred scales quadratically with the area of the coil used, which means in general that the bulk of the electrical current is generated in the largest windings of the coil. The restriction makes the application of a flat (2D) rectangular or circular coil design rather inefficient. Moreover, this restriction implies that a electronic device with a small footprint, which can merely incorporate a small coil, can hardly be recharged. A further limitation of the known electronic device is that in general the maximum energetic efficiency is obtained when the coil is oriented perpendicular to the applied magnetic field, which is commonly rather hard to achieve in case a implantable device is used which is, to certain extent, freely moveable in a body cavity.

SUMMARY OF THE INVENTION

It is an object of the invention to provide a relatively efficient electronic device.

The object is achieved according to the invention by providing an electronic device suitable for bioimplantation, comprising: at least one rechargeable power source, at least electronic component connected to said power source, and magnetoelectric conversion means connected to said power source to enable recharging of said power source, said magnetoelectric conversion means comprising a stack of at least one magnetoelastic layer and at least one piezoelectric layer, wherein said magnetoelectric conversion means has a three-dimensional geometry for receiving and magnetoelectrically converting a magnetic field originating from multiple directions respectively. The substantially improved efficiency of the electronic device is firstly due to the application of said magnetoelectric stack (laminate) of said at least one magnetoelastic layer and said at least one piezoelectric layer, preferably a stack of at least one piezoelectric layer which is sandwiched between multiple magnetoelastic layers, by means of which stack the magnetic field induced can be converted relatively efficiently into electrical energy. In case said stack is subjected to an (alternating) magnetic field the magnetoelastic layer and consequently the piezoelectric layer will be deformed resulting in the generation of an electrical current within the piezoelectric layer. The induced electrical current is subsequently used to (re)charge the power source of the electronic device. The term "magnetoelectric" thus refers to the effect in which an electric current is produced in a laminate when it is subjected to a magnetic field. The term "piezoelectric" refers to the effect in those materials which only produce an electric output when they experience a change in mechanical load. The substantially improved efficiency of the electronic device according to the invention is secondly due to the improved degree of freedom of design of the magnetoelectric conversion means, and hence of the electronic device as such, which degree of freedom is many times larger than this freedom offered by the state of the art. Due to this freedom of design the magnetoelectric conversion means is easily provided a three-dimensional geometry for receiving and magnetoelectrically converting a magnetic field originating from multiple directions respectively. In this context the term "three-dimensional geometry" implies the application of a magnetoelectric stack provided with a three-dimensional shape such that an improved probability can be obtained that at least a part of said stack is oriented substantially perpendicular to (a component of) the applied magnetic field, in order to secure the generation of sufficient electrical energy to charge the power source of the electronic device according to the invention. The risk of depletion of all electrical energy that can be provided by the power source due to (too) poor charging of the power source can thus be counteracted this way. In case the electronic device is implanted in a body cavity, the electronic device can either be fixedly attached to the body or can, to a certain extent, be freely moveably within said body cavity. Although the electronic device according to the invention will commonly be used as bioimplantable device, it would also be conceivable to apply the electronic device in other applications, for example in water treatment plants or in chemical engineering equipment such as a chemical reactors, pipelines, et cetera.

Suitable materials to be utilized as the magnetoelastic material in a magnetoelastic sensor may be any material with a non-zero magnetostriction and a high magnetoelastic coupling, such as iron-nickel alloys, rare earth metals, ferrites, such as spinel type ferrites ($Fe_3O_4$, $MnFe_2O_4$), silicon-iron alloys, many other different alloys and mixtures thereof. Soft magnetoelastic materials, alloys and mixtures thereof as well as amorphous magnetoelastic materials, alloys and mixtures thereof may be utilized. Examples of amorphous magnetoelastic alloys are metglases such as $Fe_{40}Ni_{38}Mo_4B_{18}$, e.g. Metglas 2826MB™ (Honeywell Amorphous Metals, Pittsburg, Pa., USA), $(FeCo)_{80}B_{20}$, $(CoNi)_{80}B_{20}$ and $(FeNi)_{80}B_{20}$. Other examples of suitable elastomagnetic materials are: $Ni_2MnGa$, Ni—Mn—Ga alloys, Ni—Ti alloys, Ag—Cd alloys (44/49 at. % Cd), Au—Cd alloys (46,5/50 at. % Cd), Cu—Al—Ni alloys (14/14.5 wt. % Al and 3/4.5 wt. % Ni), Cu—Sn alloys (approx. 15 at. % Sn), Cu—Zn alloys (38.5/41.5 wt. % Zn), Cu—Zn—X alloys wherein X=Si, Al or Sn; Fe—Pt alloys (approx. 25 at. % Pt), Mn—Cu alloys (5/35 at. % Cu), Fe—Mn—Si, Pt alloys, Co—Ni—Al alloys, Co—Ni—Ga alloys, Ni—Fe—Ga alloys, and Ti—Pd alloys in various concentrations. The term "magnetostriction" introduced in this paragraph refers to a phenomenon whereby a material will change dimensions in the presence of an external magnetic field. The size of the dimensional change depends on the magnetization in the material and, of course, on the material properties. The phenomenon of magnetostriction is due to the interaction between the atomic magnetic moments in the material. The piezoelectric layer is preferably selected from the group consisting of lead zirconate titanate (PZT), lead zincate niobate (PZN), lead zincate niobate lead-titanate (PZN-PT), lead magnesium niobate lead-titanate (PMN-PT), lead lanthanum zirconate titanate (PLZT), Nb/Ta doped-PLZT, barium zirconate titanate (BZT), lead metanobiate, polyvinylidene fluoride (PVFD), polyvinyl chloride (PVC), quartz, barium titanate, cadmium sulphide, topaz, tourmaline, and cane sugar. The electronic device according to the invention preferably comprises a protective casing enclosing the power source and/or the at least one electronic component at least substantially. More preferably, the casing is adapted to shield the power source and/or the electronic component against surrounding fluids, in particular body fluids, to enhance the life span of both the power source and the electronic component. The casing can further be adapted to enclose the magnetoelectric conversion means at least substantially, wherein at least a part of the magnetoelectric stack is preferably applied onto an internal surface of said casing. However, it is also imaginable that at least a part of the magnetoelectric stack is applied onto an external surface of said casing. The magnetoelectric stack may cover an entire surface of said casing. However, it is also conceivable that the magnetoelectric stack merely covers a casing surface partially, wherein a remaining part of said casing surface is left uncovered. Application of the stack onto a casing surface is preferably realised by successive deposition of the stack layers by means of one of the following (known) techniques: chemical vapour deposition (CVD), physical vapour deposition (PVD), atomic layer deposition (ALD), sol-gel (impregnation) techniques, melt casting, die casting, spray coating, or flash evaporation. In an alternative preferred embodiment the casing is formed by the magnetoelectric conversion means. By smartly integrating the casing with the magnetoelectric stack a further improved and volume-efficient means of wireless charging is introduced. An additional important advantage is that the overall size of the power source will be smaller as (more efficient) recharging is now possible, resulting in a relatively compact and less-invasive device. The casing applied may be either rather rigid or rather flexible depending on the composition and thickness of the casing. Application of a relatively flexible casing could be particularly favourable, since external forces applied to the casing will also cause deformation of the piezoelectric layer leading to (additional) charging of the power source.

The shape of the casing applied can be of various nature. Preferably the casing has a substantially spherical pill shape or a substantially cylindrical pill shape, which shapes are commonly very well suitable to be incorporated in a human or animal body. In addition to these shapes, it is also imaginable to apply a casing having a round pill shape, an ellipsoidal shape, an elongated capsule shape, an oval, cylindrical shape, an elongated ellipsoid shape, an elongated rectangular shape, a super elliptical cylindrical shape, a hexagonal cylindrical shape, and an octagonal cylindrical shape, a triangular, cylindrical pill shape, a cardioid cylindrical pill shape, a hexagonal cylindrical pill shape, or any other polyhedron.

The power source applied preferably comprises at least one solid-state battery, and more preferably a thin film battery comprising a substrate, and at least one battery stack deposited onto said substrate, the battery stack comprising: a first battery electrode, a second battery electrode, and an intermediate solid-state electrolyte separating the first battery electrode and the second battery electrode. Preferably, at least one battery electrode of the power source is adapted for storage of active species of at least one of following elements: hydrogen (H), lithium (Li), beryllium (Be), magnesium (Mg), aluminium (Al), copper (Cu), silver (Ag), sodium (Na) and potassium (K), or any other suitable element which is assigned to group 1 or group 2 of the periodic table. So, the power source of the electrical device according to the invention may be based on various intercalation mechanisms and is therefore suitable to form different kinds of batteries, e.g. Li-ion batteries, NiMH batteries, et cetera. In a preferred embodiment at least one battery electrode, more preferably the battery anode, comprises at least one of the following materials: C, Sn, Ge, Pb, Zn, Bi, Sb, Li, and, preferably doped, Si. A combination of these materials may also be used to form the battery electrode(s). Preferably, n-type or p-type doped Si is used as battery electrode, or a doped Si-related compound, like SiGe or SiGeC. Also other suitable materials may be applied as battery anode, preferably any other suitable element which is assigned to one of groups 12-16 of the periodic table, provided that the material of the battery electrode is adapted for intercalation and storing of the above-mentioned reactive species. The aforementioned materials are in particularly suitable to be applied in lithium ion batteries. In case a hydrogen based energy source is applied, the battery anode preferably comprises a hydride forming material, such as $AB_5$-type materials, in particular $LaNi_5$, and such as magnesium-based alloys, in particular $Mg_xTi_{1-x}$. The battery cathode for a lithium ion based energy source preferably comprises at least one metal-oxide based material, e.g. $LiCoO_2$, $LiNiO_2$, $LiMnO_2$ or a combination of these such as. e.g. $Li(NiCoMn)O_2$. In case of a hydrogen based energy source, the battery cathode preferably comprises $Ni(OH)_2$ and/or $NiM(OH)_2$, wherein M is formed by one or more elements selected from the group of e.g. Cd, Co, or Bi. Further embodiments are disclosed in the international application WO 2008/032252 in the name of applicant. All patents, patent applications, and literature references cited in this specification are hereby incorporated herein by reference in their entirety. Alternatively the power source may comprise at least one capacitor to power the electronic component of the electronic device according to the invention. Several types of capacitors can be used among which wet/dry capacitors, elcos, supercaps, ultracaps, et cetera.

In a preferred embodiment the electrical component comprises at least one component chosen from the following group of components: a sensor, such as a temperature sensor or an acidity sensor, a transmitter, a receiver, a camera, an actuator, and a pump. By means of these electronic components a wide range of applications of the electronic device according to the invention can be realised, among which drug delivery devices, neuro-stimulators, (bio)sensors, transmitters, receivers, and/or actuators.

The electronic device commonly comprises a power management system connected to both the power source and the magnetoelectric conversion means. The primary function of said power management system is to optimise a relatively quick and safe (re)charging process of the power source dependent on the characteristics of said power source. The power management typically comprises an electric convertor (DC-DC or AC-DC) to convert the voltage induced within the magnetoelectric means to a desired voltage for the power source to be charged. By means of a (micro)controller one or multiple charging parameters can be measured, such as the charging current, the charging voltage, and the temperature. Based upon these measurements the charging process can eventually be manipulated and hence further be optimized. Optionally, the power management system comprises a second converter for converting the voltage of the power source to the voltage requirement by the electric component powered by said power source. In case this second converter is applied, the (micro)controller preferably also checks the voltage provided to the electric component in order to be able to prevent said voltage to drop below a minimum voltage required by said electric component.

The invention also relates to an assembly of an electronic device according to the invention and a charging unit adapted to generate a magnetic field, preferably an alternating magnetic field. The charging unit commonly comprises one or multiple coils to induce the magnetic field.

BRIEF DESCRIPTION OF THE DRAWINGS

The invention is illustrated by way of the following non-limitative examples, wherein.

DETAILED DESCRIPTION OF THE EMBODIMENTS

Figure 1:
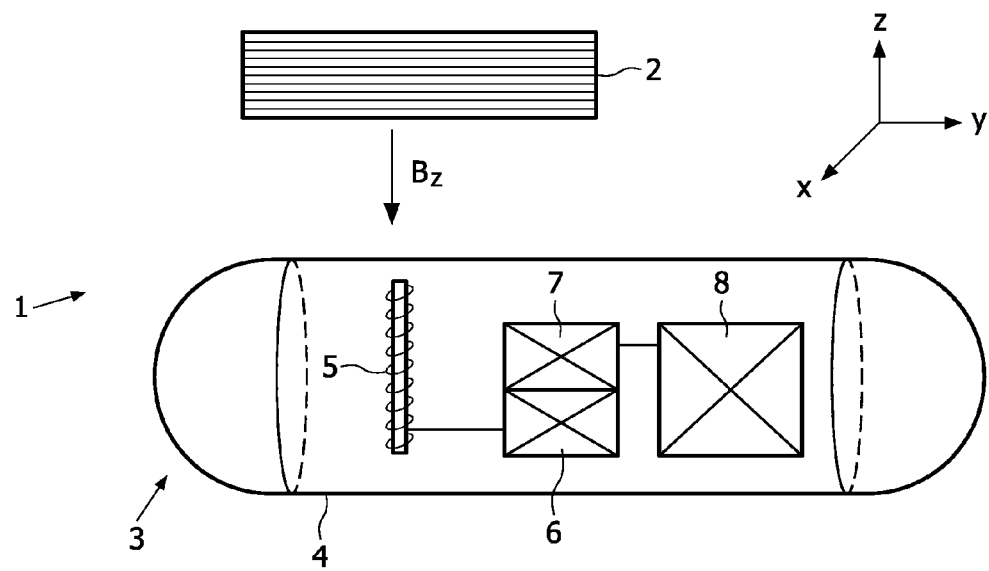
FIG. 1 shows a schematic cross section of an assembly of a magnetic charging unit and a bioimplantable electronic device known from the prior art.

FIG. 1 shows a schematic cross section of an assembly 1 of a magnetic charging unit 2 and a bioimplantable electronic device 3 known from the prior art. The known device 3 comprises a cylindrical pill shaped housing 4 enclosing a coil 5, a power management system 6 connected to said coil 5, a rechargeable battery 7 connected to said power management system 6, and an electronic component 8, such as a sensor, connected to said battery 7. By means of the charging unit 2 an alternating magnetic field B is imposed to the electronic device 3. The coil 5 will convert the magnetic field B into electrical energy which is used to (re)charge the battery 7. A first drawback of the known device 3 is that by means of the coil 5 merely a relatively poor and inefficient transfer of energy within the device 3 can be achieved. Moreover, the coil 5 is substantially sensitive for a magnetic field $B_z$ which is perpendicular to each winding of the coil 5. In case the magnetic field would originate from another direction than the z-direction, this would further deteriorate or even cease the charging process.

Figure 2:
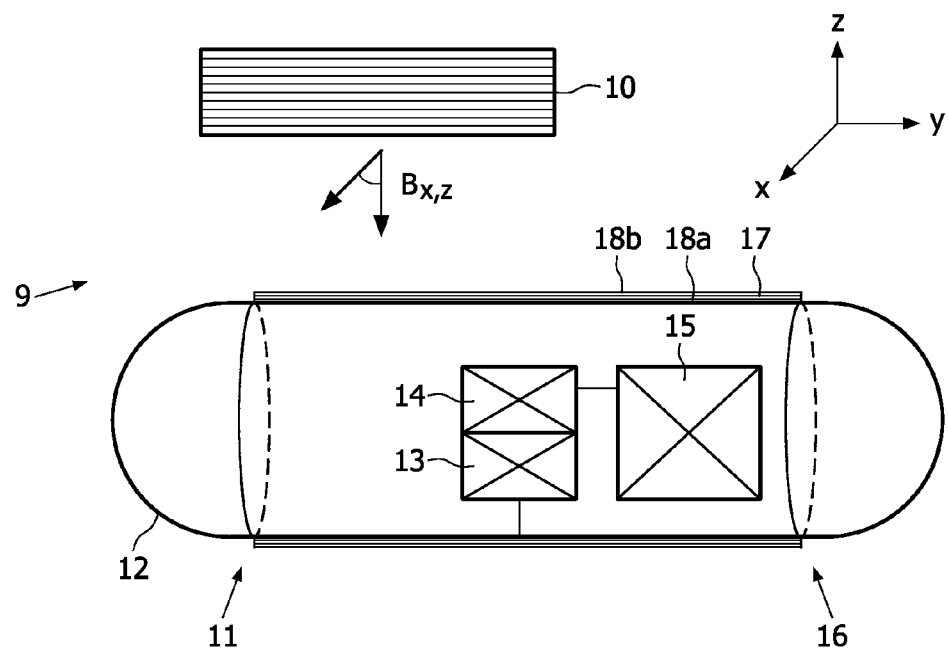
FIG. 2 shows a schematic cross section of an assembly of a magnetic charging unit and a bioimplantable electronic device according to the invention.
Figure 3:
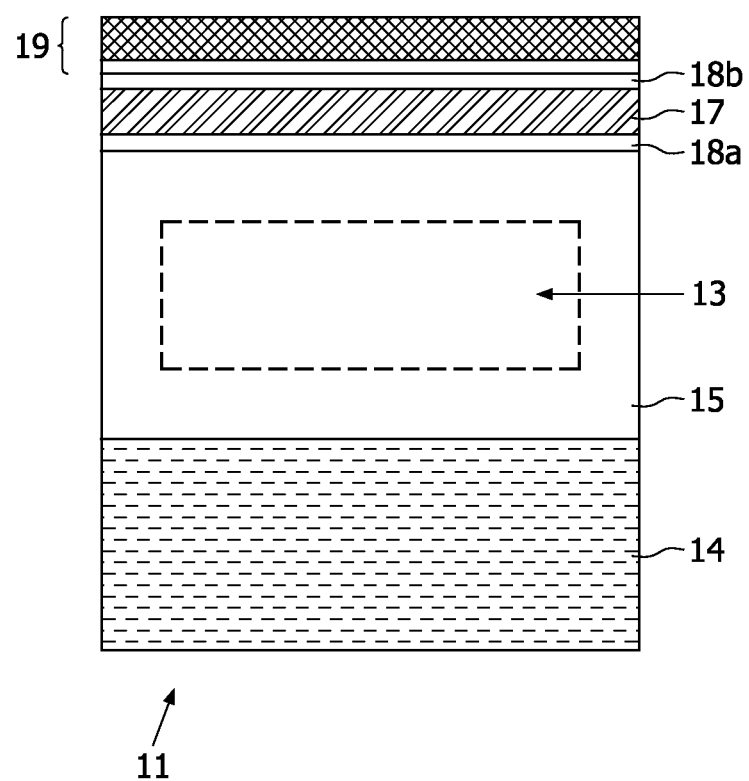
FIG. 3 shows an alternative schematic view of the electronic device according to FIG. 2.

FIG. 2 shows a schematic cross section of an assembly 9 of a magnetic charging unit 10 and a bioimplantable electronic device 11 according to the invention. The charging unit 10 commonly comprises one or multiple coils (not shown) to induce a magnetic field B. The device 11 according to the invention comprises a cylindrical pill shaped housing 12 enclosing a power management system 13, a rechargeable solid-state battery 14 connected to said power management system 13, and an electronic component 15, such as a sensor, connected to said battery 14. An external surface of the housing 12 is partially covered with a magnetoelectric laminate 16 comprising a piezoelectric layer 17 sandwiched in between two magnetoelastic layers 18a, 18b. The magnetoelectric laminate 16 is coupled to the power management system 13. The magnetoelectric laminate 16 is deposited onto the housing 12 by means of conventional techniques. As shown in this figure the magnetoelectric laminate 16 has a three-dimensional shape as a result of which said laminate 16 is adapted to efficiently convert a magnetic field B originating from the x-direction and/or the z-direction. In case the external surface of the housing 12 would be covered completely by the laminate 16, then laminate 16 would also be adapted to efficiently convert a magnetic field B originating from the y-direction. This makes the orientation of the device 11 with respect to the charging unit 10 less critical, and improves and secures the charging process of the battery 14. An alternative schematic view of the electronic device 11 is shown in FIG. 3, wherein the device 11 is shown as a stack of the battery 14, the electrical component 15 incorporating said power management system 13, and the magnetoelectric laminate 16. As also shown in this figure the magnetoelectric laminate 16 is covered by a biocompatible coating 19. Furthermore it is clearly shown in this figure that the piezoelectric layer 17 is enclosed by two magnetoelastic layers 18a, 18b.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The mere fact that certain measures are recited in mutually different dependent claims does not indicate that a combination of these measures cannot be used to advantage.

The invention claimed is:

1. An electronic device suitable for bio implantation, comprising:
    at least one rechargeable power source;
    at least electronic component connected to said power source; and
    magnetoelectric conversion means connected to said power source to enable recharging of said power source, said magnetoelectric conversion means comprising at least one stack of at least one magnetoelastic layer and at least one piezoelectric layer,
    wherein said magnetoelectric conversion means has a three-dimensional surface geometry, such that a part of the at least one stack is oriented substantially perpendicular to a magnetic field, originating from multiple directions, respectively, for receiving and magnetoelectrically converting the magnetic field to electrical energy for recharging of said power source.

2. The electronic device according to claim 1, wherein the magnetoelectric conversion means comprises a stack of at least one piezoelectric layer which is sandwiched between multiple magnetoelastic layers.

3. The electronic device according to claim 1, wherein the magnetoelastic layer is made of at least one following materials: iron-nickel alloys, rare earth metals, ferrites, in particular spinel type ferrites, and silicon-iron alloys.

4. The electronic device according to claim 1, wherein the piezoelectric layer is selected from the group consisting of lead zirconate titanate (PZT), lead zincate niobate(PZN), lead zincate niobate lead-titanate (PZN-PT), lead magnesium niobate lead-titanate (PMN-PT), lead lanthanum zirconate titanate (PLZT), Nb/Ta doped-PLZT, barium zirconate titanate (BZT), lead metanobiate, polyvinylidene fluoride (PVFD), polyvinyl chloride (PVC), quartz, barium titanate, cadmium sulphide, topaz, tourmaline, and cane sugar.

5. The electronic device according to claim 1, wherein the electronic device comprises a casing enclosing at least one of the power source and the electronic component at least substantially.

6. The electronic device according to claim 5, wherein the casing further encloses at least a part of the magnetoelectric stack.

7. The electronic device according to claim 5, wherein at least a part of the magnetoelectric stack is applied onto an external surface of said casing.

8. An electronic device suitable for bio implantation, comprising:
   at least one rechargeable power source;
   at least electronic component connected to said power source;
   magnetoelectric conversion means connected to said power source to enable recharging of said power source, said magnetoelectric conversion means comprising at least one stack of at least one magnetoelastic layer and at least one piezoelectric layer; and
   a casing enclosing at least one of the power source and the electronic component at least substantially,
   wherein said magnetoelectric conversion means has a three-dimensional surface geometry, such that a part of the at least one stack is oriented substantially perpendicular to a magnetic field, originating from multiple directions, respectively, for receiving and magnetoelectrically converting the magnetic field to electrical energy for recharging of said power source, and
   wherein the casing is formed by the magnetoelectric conversion means.

9. The electronic device according to claims 5, wherein the casing has a substantially spherical shape or a substantially cylindrical pill shape.

10. The electronic device according to claim 1, wherein the power source comprises at least one solid-state battery.

11. The electronic device according to claim 1, wherein the power source comprises at least one capacitor.

12. The electronic device according to claim 1, wherein the electrical component comprises at least one component chosen from the following group of components: a sensor, a transmitter, a receiver, a camera, an actuator, and a pump.

13. The electronic device according to claim 1, wherein the electronic device comprises a power management system connected to both the power source and the magnetoelectric conversion means.

14. An assembly comprising the electronic device according to claim 1 and a charging unit configured to generate the magnetic field.

15. An electronic device configured for bio implantation, the electronic device comprising:
   a power source;
   an electronic component powered by the power source;
   a casing configured to contain the power source and the electronic component; and
   a magnetoelectric stack comprising at least one magnetoelastic layer and at least one piezoelectric layer, and configured to convert a magnetic field into electrical energy for charging of the power source,
   wherein the magnetoelectric stack is applied to a surface of the casing and at least partially surrounds at least one of the power source and the electric component, increasing a probability that at least a portion of the magnetoelectric stack is oriented substantially perpendicular to at least one component of the magnetic field for converting into the electrical energy.

16. The electronic device according to claim 15, further comprising:
   a power management system contained within the casing and connected to the power source and the magnetoelectric stack, the power management system being configured to optimize charging the power source.

17. The electronic device according to claim 16, wherein the power management system comprises one of a DC-DC converter or an AC-DC converter to convert the electrical energy produced by the magnetoelectric stack to a desired voltage for the charging power source.

18. The electronic device according to claim 15, wherein the electrical component comprises at least one of a sensor, a transmitter, a receiver, a camera, an actuator, and a pump.

19. The electronic device according to claim 15, wherein the magnetoelectric stack is applied to an inner surface casing.

20. The electronic device according to claim 15, wherein the magnetoelectric stack is applied to an outer surface of the casing.

* * * * *